(12) United States Patent
Galun et al.

(10) Patent No.: US 7,461,539 B2
(45) Date of Patent: Dec. 9, 2008

(54) QUARTZ CRYSTAL MICROBALANCE HUMIDITY SENSOR

(75) Inventors: Ehud Galun, Rehovot (IL); Galit Zilberman, Rishon Lezion (IL); Vladimir Tsionsky, Rehovot (IL); Eliezer Gileadi, Herzlia (IL)

(73) Assignees: Elop Electro-Optics Industries Ltd., Rehovot (IL); Ramot at Tel Aviv University Ltd., Tel Aviv (IL)

( * ) Notice: Subject to any disclaimer, the term of this patent is extended or adjusted under 35 U.S.C. 154(b) by 368 days.

(21) Appl. No.: 10/558,148

(22) PCT Filed: May 17, 2004

(86) PCT No.: PCT/IL2004/000418

§ 371 (c)(1),
(2), (4) Date: Jan. 23, 2006

(87) PCT Pub. No.: WO2004/104567

PCT Pub. Date: Dec. 2, 2004

(65) Prior Publication Data

US 2006/0260385 A1 Nov. 23, 2006

Related U.S. Application Data

(60) Provisional application No. 60/473,043, filed on May 22, 2003.

(51) Int. Cl.
*G01N 29/02* (2006.01)
(52) U.S. Cl. ..................................... 73/24.04
(58) Field of Classification Search ................. 73/24.04
See application file for complete search history.

(56) References Cited

U.S. PATENT DOCUMENTS

| | | | | |
|---|---|---|---|---|
| 5,695,925 A | * | 12/1997 | Ebersole et al. | 435/4 |
| 5,756,279 A | * | 5/1998 | Ebersole et al. | 435/4 |
| 5,827,947 A | * | 10/1998 | Miller et al. | 73/24.06 |

FOREIGN PATENT DOCUMENTS

EP 0 992 768 A2 4/2000

OTHER PUBLICATIONS

Wei, Jian, et al., "In-Line Moisture Monitoring in Semiconductor Process Gases by a Reactive-Metal-Coated Quartz Crystal Microbalance", Journal of the IES, Mar. 1997, vol. 40, No. 2, pp. 43-48.

Galatsis, et al., "Quartz Crystal Microbalance Humidity Sensor with Porous Electrodes", Optoelectronic and Microelectronic Materials Devices, Proceedings 1998, Conference on Perth, WA, Australia, Dec. 14-16, 1998, pp. 373-375.

(Continued)

*Primary Examiner*—Hezron Williams
*Assistant Examiner*—Rodney T Frank
(74) *Attorney, Agent, or Firm*—Darby & Darby PC (57) ABSTRACT

A humidity sensor and a quartz crystal microbalance (QCM) therefor, for measuring low humidity levels, and a method for preparing same. The metallic surface of the QCM is electroplated with a hygroscopic layer. The hygroscopic layer preferably includes Manganese. A salt is formed on the hygroscopic layer. The salt is preferably salt of Manganese, and most preferably Manganese Chloride (MnCl2).

13 Claims, 8 Drawing Sheets

OTHER PUBLICATIONS

Pascal-Delannoy, F., et al., "Quartz Crystal Microbalance (QCM) used as a Humidity Sensor", Sensors and Actuators A, Sep. 1, 2000, vol. 84, No. 3, pp. 285-291.

International Search Report and Written Opinion mailed Sep. 22, 2004 in PCT/IL2004/000418.

* cited by examiner

QUARTZ CRYSTAL MICROBALANCE HUMIDITY SENSOR

CROSS-REFERENCE TO PRIOR APPLICATION

This is a U.S. National Phase application under 35 U.S.C. 371 of International Patent Application No. PCT/IL2004/000418, filed May 17, 2004, and claims the benefit of Provisional Application Serial No. 60/473,043, filed May 22, 2003, which is incorporated by reference herein. The International Application was published in English on Dec. 2, 2004 as WO 2004/104567 A1 under PCT Article 21(2).

FIELD OF THE DISCLOSED TECHNIQUE

The disclosed technique relates to humidity sensors in general, and to a QCM based humidity sensor for the low humidity range, in particular.

BACKGROUND OF THE DISCLOSED TECHNIQUE

There is a need for methods of measuring low humidity levels in the fields of microelectronic, communication and electro-optical systems. Relatively low levels of humidity can cause degradation in the performance of these systems and in some cases may cause irreversible damage. New communication systems should work with high reliability for long periods of time without requiring maintenance. In these systems, the ability to perform maintenance activity is limited and therefore such maintenance should be done only when necessary.

Many electro-optical systems are sensitive to humidity and therefore their maintenance includes a periodic drying operation. Such a drying operation is usually done without taking into account the precise humidity level of the system. As the technology of electro-optical systems develop towards higher energy density and lower temperature, the humidity level and contamination level is expected to decrease accordingly. When the temperature is low, water vapor can condense on the surface of an optical device, thereby forming a water droplet. This droplet may act as a lens that focuses the energy of the laser, causing physical damage to the optical device. Other examples of less severe damage which may result include inferior system performance and longer delay times.

A humidity sensor integrated into a system can be used to warn of the presence of high humidity that can be hazardous to the system. The humidity sensor may further indicate the need for drying. The humidity sensor must be small, light and reliable. There are many commercially available humidity sensors. Each type of sensor usually meets the requirements of a certain market or application. However, there is no single sensor that is suitable for all requirements and for every humidity range.

There are currently few technologies that measure low humidity levels. The most popular system is based on the diffusion of water vapor into a solid state material, such as $Al_2O_3$. This sensor acts as a capacitor. The number of water molecules absorbed determines the electrical impedance of the capacitor, which is proportional to the vapor pressure. Although such sensors are popular, systems for measuring low humidity level are very expensive. Moreover, these systems cannot be manufactured with great consistency and interchangeability. They also exhibit varying degree of aging and hysteresis (delayed response).

The most reliable system is known as chilled mirror hygrometers. The measurement in this sensor is done by directing a light beam onto a mirror using a diode laser. The mirror then reflects the light beam onto a photo detector. If the mirror is dry, nearly all of the light which has reached the mirror is received by the photo detector. However, with the presence of dew on the mirror, the reflective characteristic of the mirror changes and the light reflected off the mirror is diffused, thus reducing the amount of light reaching the photo detector. The mirror is in thermal contact with a chiller which is capable of cooling the mirror below dew point. The system is set up to find the exact temperature on the mirror at which the first dew is formed. This temperature corresponds exactly to the dew point. This method is very sensitive, but cumbersome and expensive to implement and maintain.

Similar systems are based on surface acoustic waves (SAW). These sensors utilize SAW devices to detect the presence of moisture. The SAW sensor generates surface acoustic waves which are transmitted through a delay path using the reversed piezoelectric effect. Condensation forms on the surface of the SAW device, which attenuates the wave and alters its velocity. The SAW device is cooled as in the chilled mirror technology, and the SAW temperature at which the wave changes its properties is the dew point. Such systems are extremely sensitive, but very complex and expensive.

Other piezoelectric sensors are based on Quartz Crystal Microbalance (QCM) technology. A commercial QCM system measures moisture by monitoring the vibration frequency change of a coated quartz crystal that is alternately exposed to wet and dry gas. A gas sample is divided into two streams, a sample stream and a reference stream, which are alternately passed across the measuring crystal. The crystal is coated with a polymer hygroscopic layer. Although this system is very accurate, can measure very low humidity levels, and has a fast response time, the system is also very expensive and not suitable for in-situ applications.

Another humidity sensor utilizes a coating on a restrained or non-vibrating cantilever beam. Changes in water vapor pressure cause stress in the coating and the beam. This stress is measured to provide an indication of the vapor pressure. This is a sensitive humidity sensor, but not for very low humidity levels.

There is therefore a need for a reliable humidity sensor for the lower humidity range, which is small, simple and inexpensive.

SUMMARY OF THE PRESENT DISCLOSED TECHNIQUE

In accordance with the disclosed technique, there is thus provided a humidity sensor and a quartz crystal microbalance (QCM) therefor, for measuring low humidity levels. A metallic surface of the QCM is electroplated with a hygroscopic layer. The metallic surface of the QCM may include gold. The hygroscopic layer preferably includes Manganese. A salt is formed on the hygroscopic layer. The salt is preferably salt of Manganese, and most preferably Manganese Chloride ($MnCl_2$).

According to another aspect of the disclosed technique, there is also provided a method for the preparation of a QCM for a humidity sensor for measuring low humidity levels. The method includes electroplating a metallic surface of the QCM with a hygroscopic layer and forming a salt on the hygroscopic layer. The metallic surface of the QCM preferably includes gold. The electroplating is preferably conducted with a highly hygroscopic inorganic compound, and most preferably with Manganese. Preferably, the forming of salt includes forming a salt of Manganese Chloride ($MnCl_2$).

Further preferably, the electroplating includes preparing a solution containing 0.2M $MnCl_2$ and 1M $NH_4OH$, and plating at 0.15 $A/cm^2$ until a metal film thickness of 8 μm is achieved. The forming of salt preferably includes exposing the $MnCl_2$ to wet hydrochloride (HCl) vapors formed over a solution of concentrate (fuming) solution of HCl, held at 0° C., for 5 minutes, and drying in a vacuum at 50° C. The vapor pressure of the HCl is preferably 46 mmHg. Preferably, the QCM is dried at 50° C.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique features a low cost and highly sensitive humidity sensor for the low humidity range. The humidity sensor is based on QCM technology. The humidity sensor is sensitive in the range of −70° C. to −10° C. Dew Point. The humidity sensor exhibits relatively fast response time. The humidity sensor also exhibits good stability after high humidity exposure over a long time and temperature cycling. The small dimensions of the QCM crystal in the humidity sensor, and the relatively simple electronics required to operate the humidity sensor, make the humidity sensor suitable for in-situ use in sensitive systems. The disclosed technique further provides a method for the preparation of the QCM-based humidity sensor.

The fundamental frequency of a QCM is altered when mass is added to the surface thereof. There is a linear relationship between the mass added to the surface and the change in fundamental frequency. As the mass on the crystal increases, the fundamental frequency of the crystal decreases. The full relationship was given by Saurbrey in 1959 (G. Z. Sauerbrey, Z. Phyz. 155:206, 1959). The sensitivity of the QCM is such that a mass of only a few nanograms per square centimeter added to the surface of the QCM can be detected.

QCM are off-the-shelf products that can be purchased in a variety of shapes and fundamental frequencies. Usually the crystals are deposited with a metallic (mainly gold) layer on both sides. This layer serves as an electrical connection which is responsible for activating the crystal. This layer can also serve as a substrate for adsorption of mass, i.e.: the accumulation of a substance on the surface of a solid or a liquid.

A monolayer of water weighs approximately 40 $ng/cm^2$. The sensitivity of a 6 MHz crystal is 2 $ng/cm^2$. However water is not adsorbed on gold at low humidity levels. Therefore, there is a need to coat the active area of the crystal with a hygroscopic layer, namely—a layer capable of easily absorbing moisture. Other than being hygroscopic, the layer should preferably also satisfy additional requirements. The layer should be easy to prepare. The layer should not contaminate its surroundings (i.e., free of volatile or particle contamination). The layer should exhibit a fast response time (i.e., fast equilibrium with water vapor pressure). The layer should be easy to dry. The layer should operate over a wide temperature range. The layer should exhibit as little hysteresis as possible.

Figure 1:
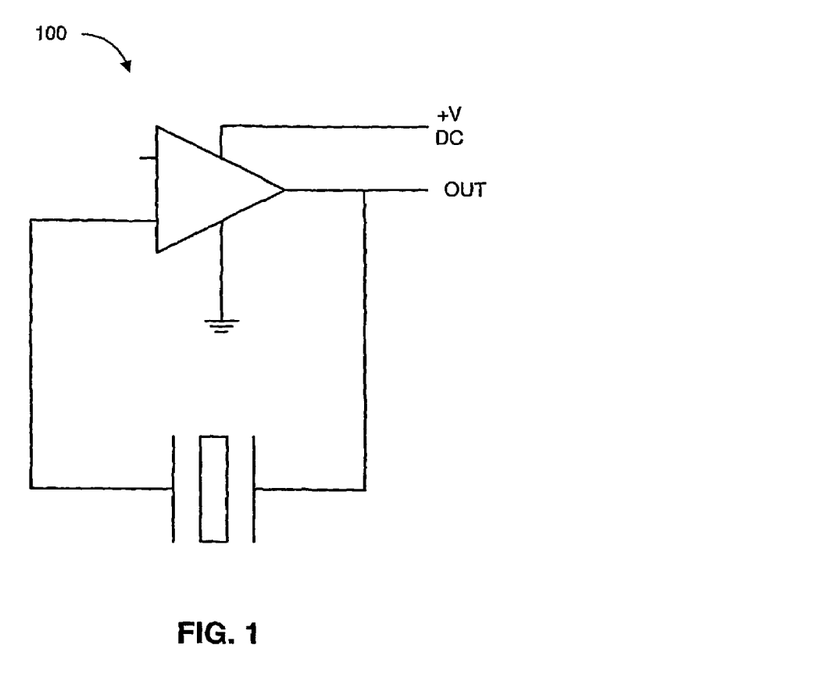
FIG. 1 is a schematic illustration of a general configuration of the controller of a QCM embedded in a humidity sensor, constructed and operative in accordance with an embodiment of the disclosed technique.
Figure 2:
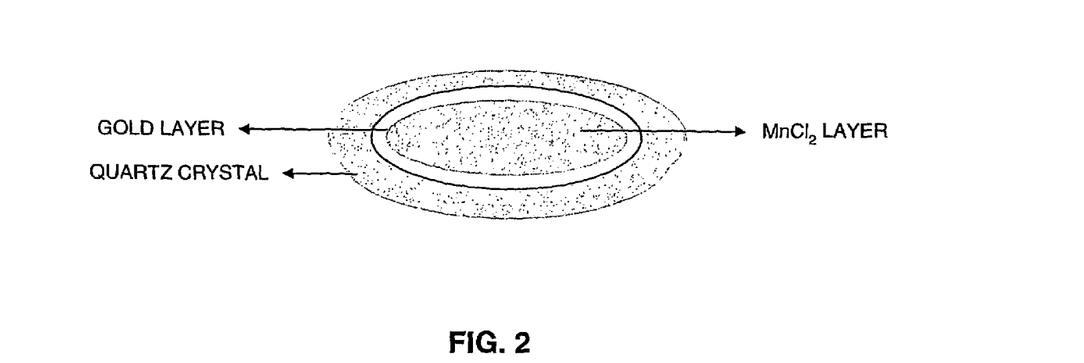
FIG. 2 is a schematic illustration of a general configuration of a QCM embedded in a humidity sensor, constructed and operative in accordance with another embodiment of the disclosed technique.

A layer that satisfies these criteria is provided pursuant to an embodiment of the disclosed technique and described below. This layer shows very high sensitivity to low humidity for a wide range of temperatures. The crystal exhibits a good response time and low hysteresis. Since the behavior of the layer depends on temperature, the temperature on the crystal is measured and a correction for temperature is made. Reference is now made to FIGS. 1 and 2. FIG. 1 is a schematic illustration of a general configuration of the controller of a QCM embedded in a humidity sensor, generally referenced 100, constructed and operative in accordance with an embodiment of the disclosed technique. FIG. 2 is a schematic illustration of a general configuration of a QCM embedded in a humidity sensor, constructed and operative in accordance with another embodiment of the disclosed technique. The gold layer of the quartz crystal is coated with a layer of Manganese Chloride ($MnCl_2$). It is noted that the QCM may be purchased already deposited with a gold layer on both sides. Alternatively, the gold layer may be deposited on the QCM before coating with the layer of $MnCl_2$. A second crystal that is not open to the surrounding environment is used as a reference crystal in order to compensate the drift of the crystal frequency with time.

Figure 3:
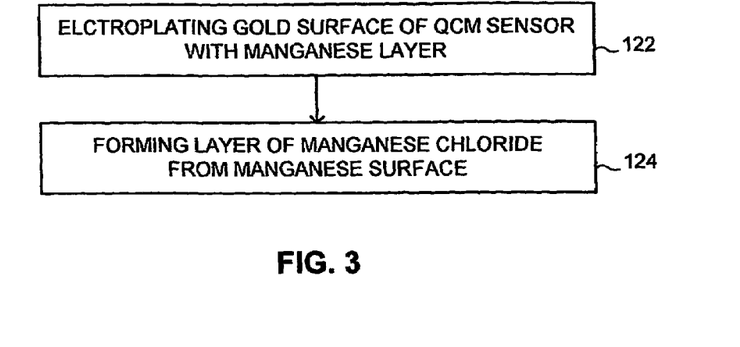
FIG. 3 is a block diagram of a method for preparation of a QCM-based humidity sensor, operative in accordance with a further embodiment of the disclosed technique.

Reference is now made to FIG. 3, which is a block diagram of a method for preparation of a QCM-based humidity sensor, operative in accordance with a further embodiment of the disclosed technique. It is noted that the following description of the disclosed technique is based on a commercial 6 MHz crystal manufactured by INFICON Holding AG ("Inficon").

However, the disclosed technique is applicable to other types of commercial crystals as well. The crystals are gold coated. The method chosen is based on a highly hygroscopic inorganic compound, specifically salt of manganese.

In procedure 122, the gold surface of the QCM sensor is electroplated with manganese. A solution containing 0.2M $MnCl_2$ and 1M $NH_4OH$ can be employed. Plating can be conducted at 0.15 A/$cm^2$. The resulting frequency shift is about 0.50 MHz, which corresponds to 6 mg/$cm^2$, or a metal film thickness of 8 µm, assuming bulk density of manganese.

In procedure 124, a layer of $MnCl_2$ is formed. At this stage the manganese (Mn) surface is exposed to wet hydrochloride (HCl) vapors formed over a solution of concentrate (fuming) solution of HCl, held at 0° C. The vapor pressure of HCl under these conditions is 46 mmHg.

The QCM coated with Mn on gold is exposed to HCl in the above manner for 5 minutes, and then dried in a vacuum at 50° C. This treatment results in a decrease of frequency of about 3.5 kHz, which is equivalent to the formation of 0.6 µmole of $MnCl_2$ and thickness of 0.26 µm, assuming a density of 2.98 g/$cm^3$ for the anhydrous $MnCl_2$. Drying the sensor at 50° C. in a vacuum may be required in order to reduce the width of the resonance from an initial value of 7-12 kHz to the desired value of 70-100 Hz.

Figure 4:
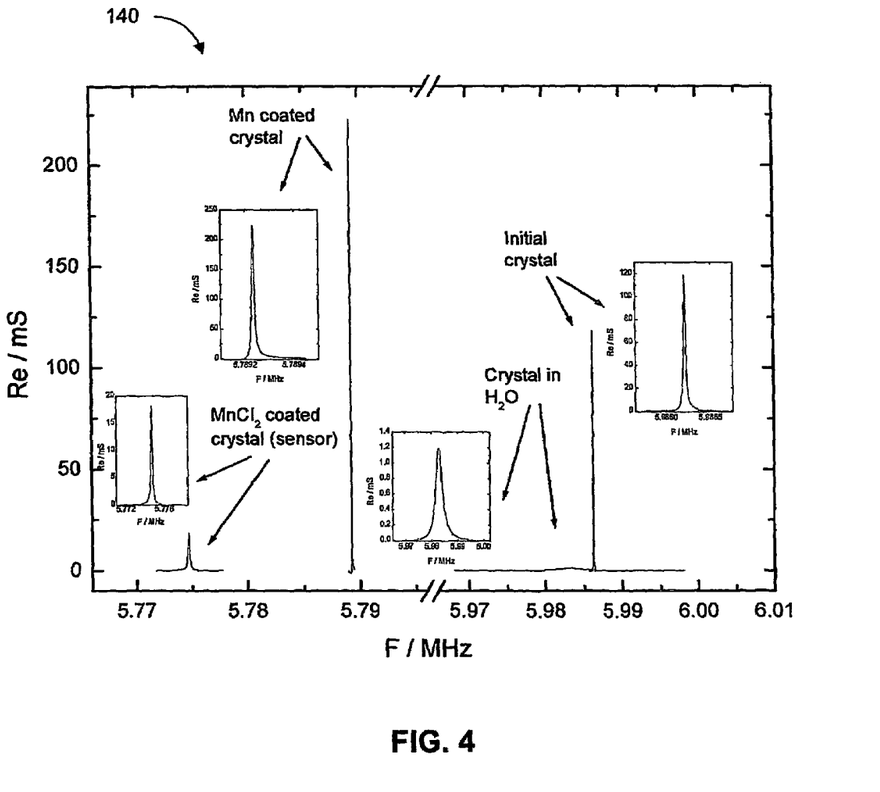
FIG. 4 is a graph of the real part of admittance as a function of frequency for QCM crystals in different stages during the preparation of the QCM-based humidity sensor of FIG. 3.

Reference is now made to FIG. 4, which is a graph, generally referenced 140, of the real part of admittance as a function of frequency for QCM crystals in different stages during the preparation of the QCM-based humidity sensor of FIG. 3. Graph 140 depicts further details of an impedance analysis of the QCM-based humidity sensor.

For the initial situation, uncoated crystal in the air, the peak is very sharp, with a width of about 20 Hz. In comparison, the same crystal placed in water shows a much wider peak, exhibiting a width of the order of 3 kHz. The exact value depends on the roughness of the surface. Immersing the crystal in water also causes a decrease of frequency of the order of 3 kHz. This decrease in frequency is caused by the change in the viscosity of the medium, and is completely unrelated to the added weight.

Coating the crystal with manganese results in a decrease of frequency due to the increase in weight, but no significant change in width. The next stage in preparation of the humidity sensor is the creation of $MnCl_2$ on the surface (procedure 124 in FIG. 3). The increase in weight leads to a decrease in frequency. At the same time, the width of the resonance is found to increase from about 10-20 Hz on the manganese-coated crystal to about 100-200 Hz.

It is noted that these results all indicate, within experimental error, that the response of the QCM was induced only by changes of water mass absorbed. This allows the use of relatively simple, custom-made, electronic circuits that measure only the changes in the resonance frequency of the quartz crystal resonator. Although a full impedance analysis may be useful under certain conditions (for example, as a precise mode of quality control in the factory), the electronics needed to measure the change of resonance frequency can be incorporated in the device and used routinely, even under service conditions, remote from the manufacturing source.

Figure 5:
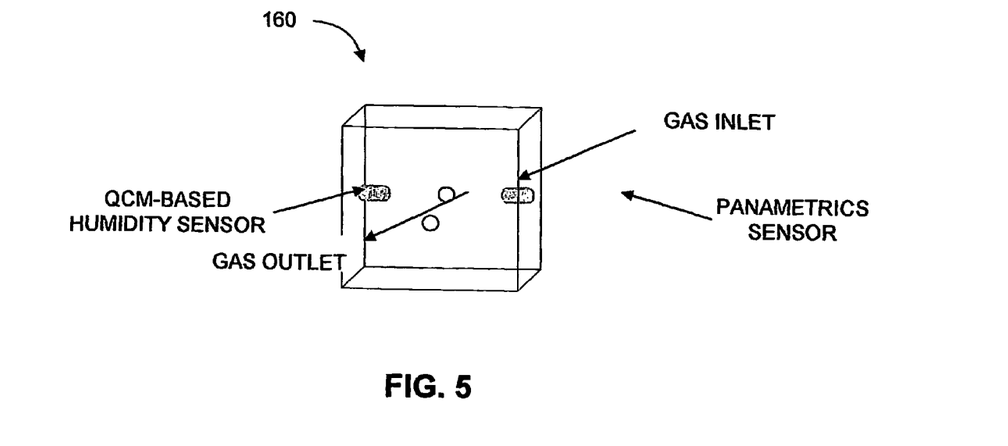
FIG. 5 is a schematic illustration of an experimental setup for the QCM-based humidity sensor of FIG. 2.

Reference is made to FIG. 5, which is a schematic illustration of an experimental setup, generally referenced 160, for the QCM-based humidity sensor of FIG. 2. Experimental setup 160 includes an aluminum box with two feed-through entrances.

The QCM-based humidity sensor can be introduced through one of the inlets and a second humidity sensor can be placed in the second entrance. The second humidity meter is directed to monitor the humidity level. A Panametrics series 2 humidity sensor can be used for the second humidity sensor.

The box also contains an inlet for passing through dry nitrogen, and an outlet in order to dry the box and to change its humidity level. The nitrogen used to dry the box has a dew point of –80° C. The box is placed in an oven so the temperature of the box could be controlled. In addition to monitoring the oven temperature, the temperature is also measured inside the box adjacent to the QCM-based humidity sensor.

Figure 6:
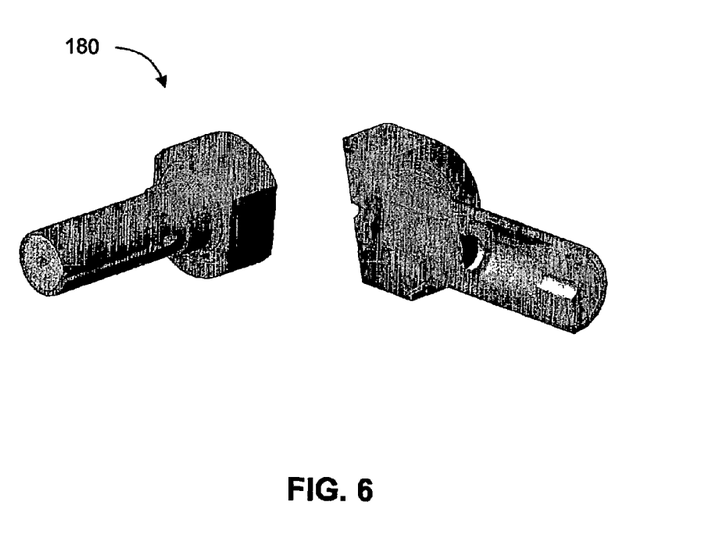
FIG. 6 is a schematic illustration of a housing for the QCM of the QCM-based humidity sensor of FIG. 2.

Reference is now made to FIG. 6, which is a schematic illustration of a housing, generally referenced 180, for the QCM of the QCM-based humidity sensor of FIG. 2. Housing 180 is designed to withstand vibrations and shocks.

The humidity level affects the response of the QCM-based humidity sensor. Humidity is presented herein below in terms of Dew Point (DP) and is shown with respect to frequency change ($\Delta f$). The value of $\Delta f=0$ is chosen as an arbitrary reference point for a DP of 0° C. where the vapor pressure is 4 mm Hg.

Figure 7:
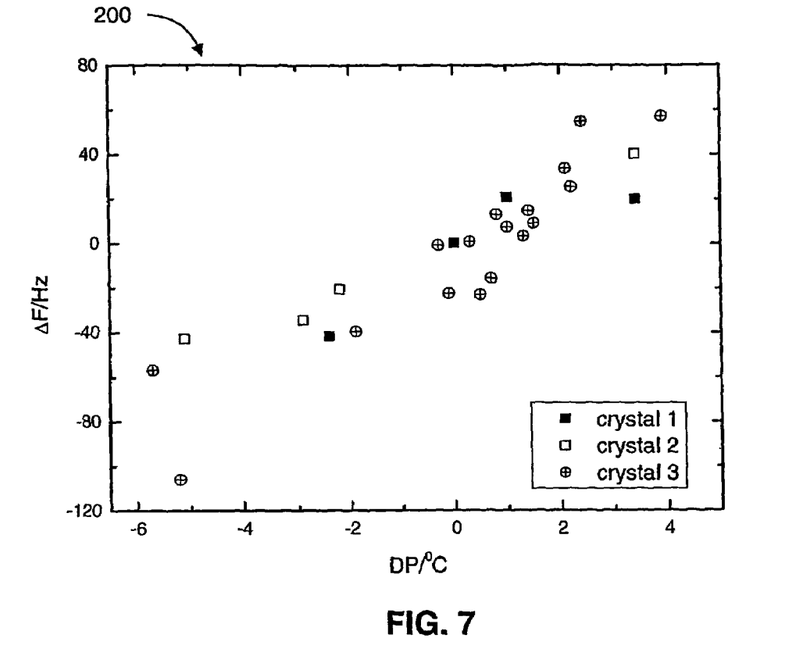
FIG. 7 is a graph of the behavior of the three QCM crystals of FIG. 4 over a range of dew points at a temperature of 70° C.
Figure 8:
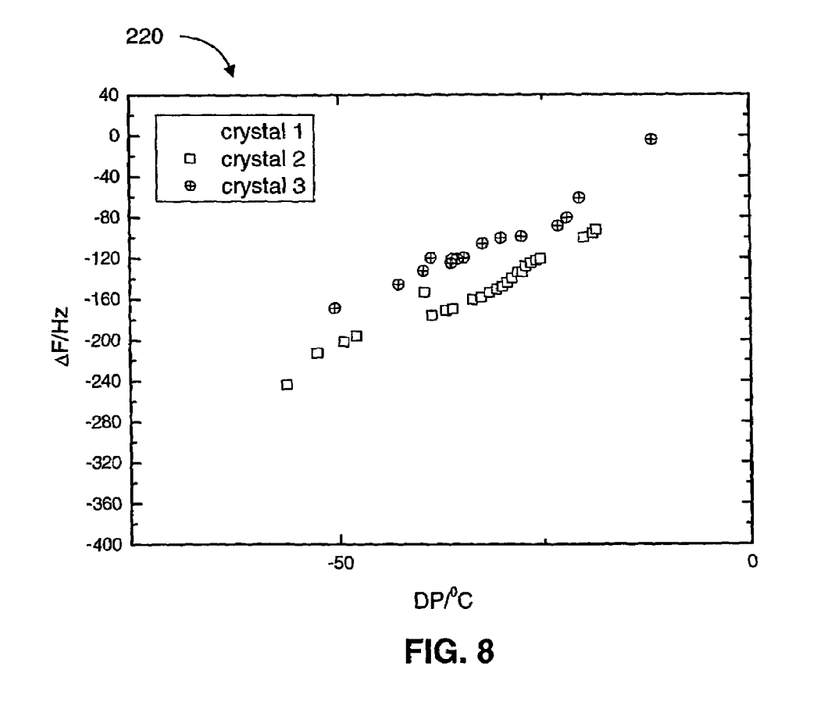
FIG. 8 is a graph of the behavior of the three QCM crystals of FIG. 4 over a range of dew points at a temperature of 24° C.
Figure 9:
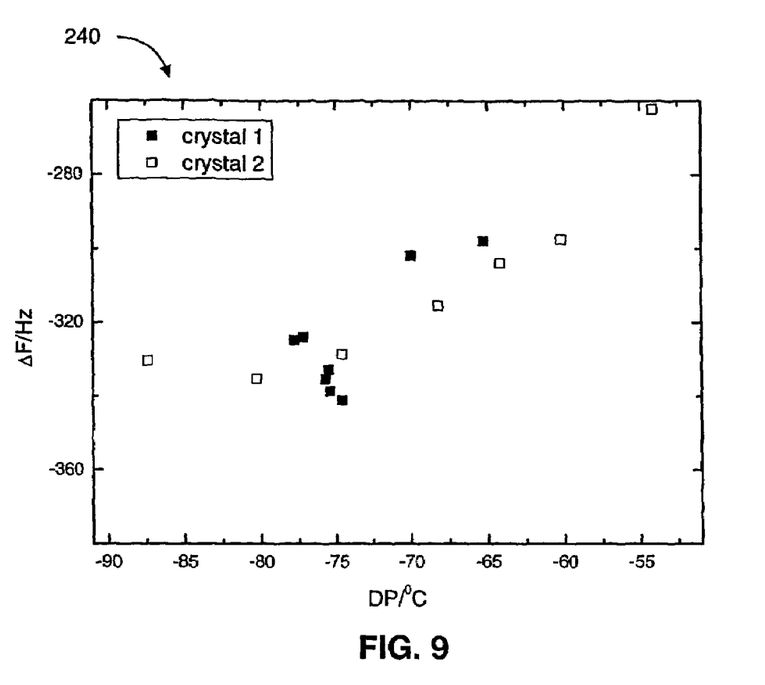
FIG. 9 is a graph of the behavior of the three QCM crystals of FIG. 4 over a range of dew points at a temperature of −20° C.

The crystals were tested immediately after their preparation at three temperatures: –20° C., 24° C. and 70° C. Reference is now made to FIGS. 7, 8 and 9. FIG. 7 is a graph, generally referenced 200, of the behavior of the three QCM crystals of FIG. 4 over a range of dew points at a temperature of 70° C. FIG. 8 is a graph, generally referenced 220, of the behavior of the three QCM crystals of FIG. 4 over a range of dew points at a temperature of 24° C. FIG. 9 is a graph, generally referenced 240, of the behavior of the three QCM crystals of FIG. 4 over a range of dew points at a temperature of –20° C.

It is noted that for all three crystals, similar behavior is obtained at the three temperatures over a range of dew points. The change in frequency over the range of dew points measured from 0° C. is greater than 200 Hz. Considering the amount of $MnCl_2$ formed initially, and assuming that the $MnCl_2$ was in the form of $MnCl_2(H_2O)_4$ at a dew point of zero, this shift indicates that essentially all the water of hydration had been removed by the time the dew point is reduced to –70° C. The sensitivity is about 3 Hz per degree change in dew point. Considering that the resolution of the measurement is 0.15 Hz, this humidity sensor should have more than enough sensitivity to detect a change in the humidity corresponding to a 1° C. change in dew point. The applicability of the humidity sensor will therefore depend on other factors, such as long term stability, stability during cycling (both in temperature and in the level of humidity), and the effect of impurities.

Figure 10:
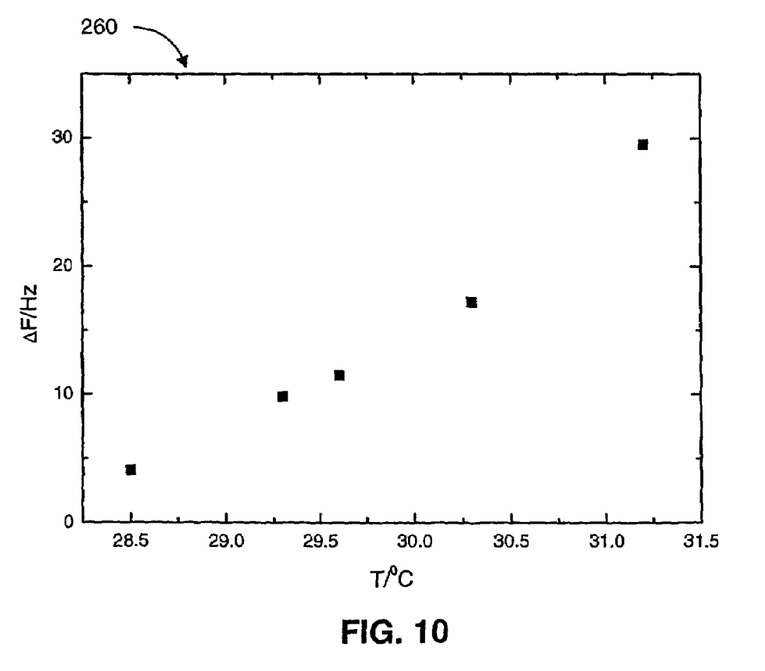
FIG. 10 is a graph of the behavior of the QCM-based humidity sensor of FIG. 2 over a range of temperatures at a dew point of −61° C.
Figure 11:
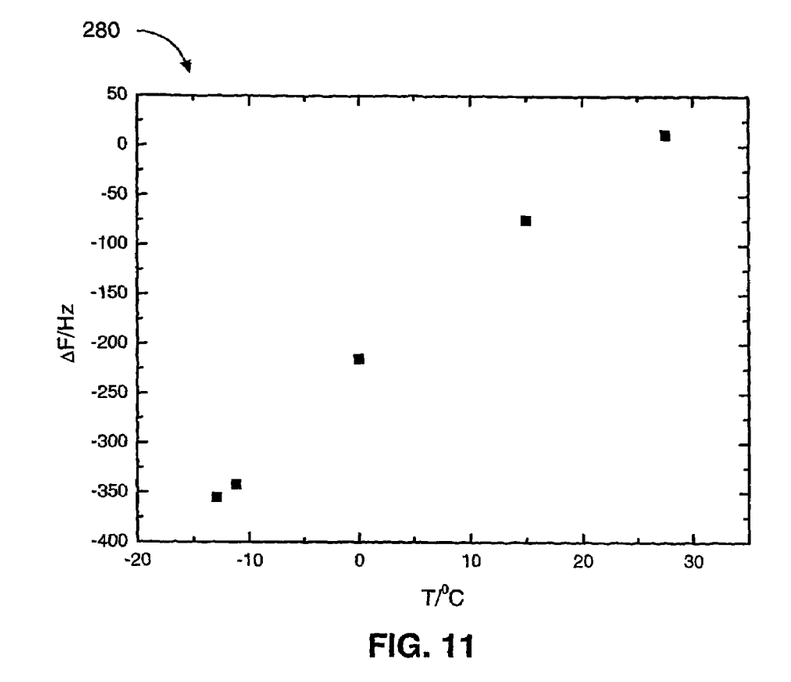
FIG. 11 is a graph of the behavior of the QCM-based humidity sensor of FIG. 2 over a range of temperatures at a dew point of −73° C.
Figure 12:
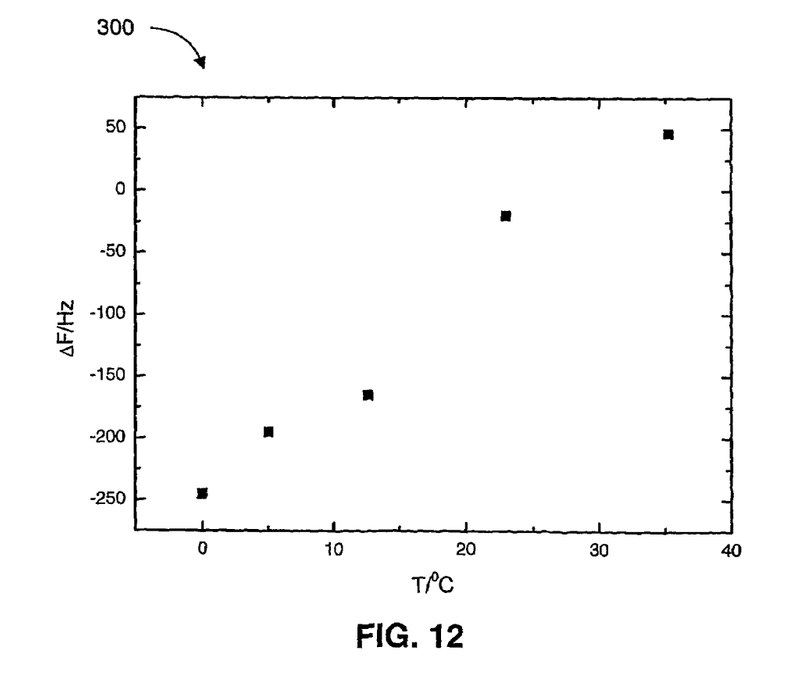
FIG. 12 is a graph of the behavior of the QCM-based humidity sensor of FIG. 2 over a range of temperatures at a dew point of −69° C.
Figure 13:
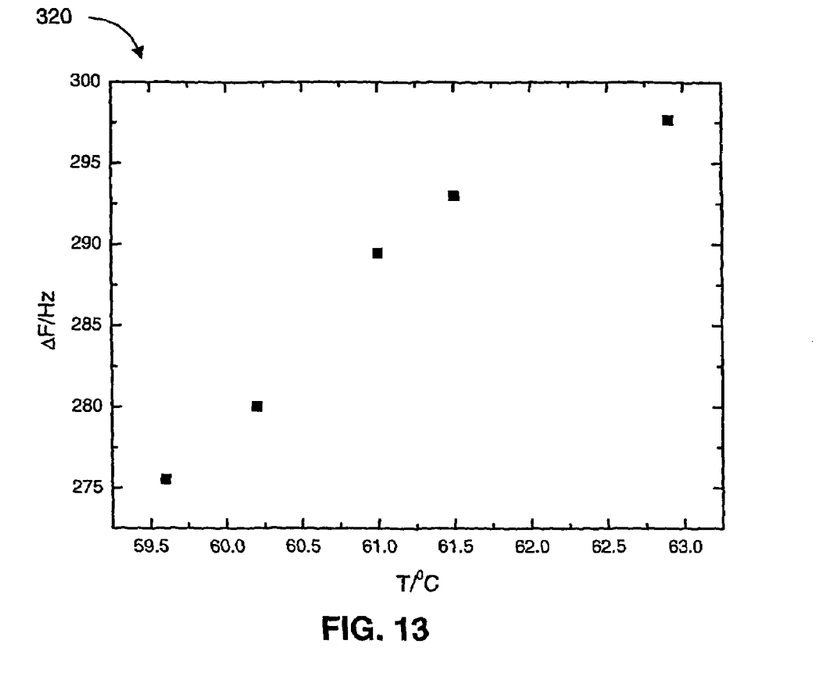
FIG. 13 is a graph of the behavior of the QCM-based humidity sensor of FIG. 2 over a range of temperatures at a dew point of −43° C.

Temperature also affects the QCM response. Reference is now made to FIGS. 10, 11, 12, and 13. FIG. 10 is a graph, generally referenced 260, of the behavior of the QCM-based humidity sensor of FIG. 2 over a range of temperatures at a dew point of –61° C. FIG. 11 is a graph of the behavior, generally referenced 280, of the QCM-based humidity sensor of FIG. 2 over a range of temperatures at a dew point of –73° C. FIG. 12 is a graph, generally referenced 300, of the behavior of the QCM-based humidity sensor of FIG. 2 over a range of temperatures at a dew point of –69° C. FIG. 13 is a graph, generally referenced 320, of the behavior of the QCM-based humidity sensor of FIG. 2 over a range of temperatures at a dew point of –43° C.

The QCM crystal in the QCM-based humidity sensor exhibits a linear response to temperature changes. This indicates that there is no inherent instability of the humidity sensor. This is an important observation since it allows for easy correction of the observed shift in frequency, which might have to be measured under field conditions, over a range of different temperatures.

In aging experiments, in which a crystal was stored in a laboratory environment and exposed to wide changes in relative humidity (up to 95%) at room temperature for several months, the properties of the humidity sensor remain unchanged. The humidity sensor could be returned to an environment in which the relative humidity is as low as DP of −70° C., without any significant changes in the frequency response thereof.

Figure 14:
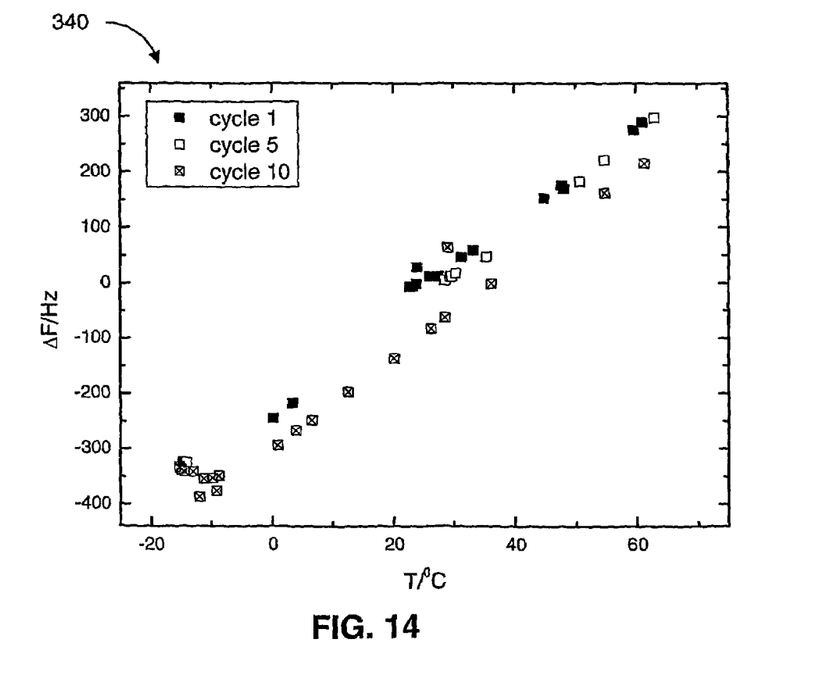
FIG. 14 is a graph of the behavior of the QCM-based humidity sensor of FIG. 2 during temperature cycling.
Figure 15:
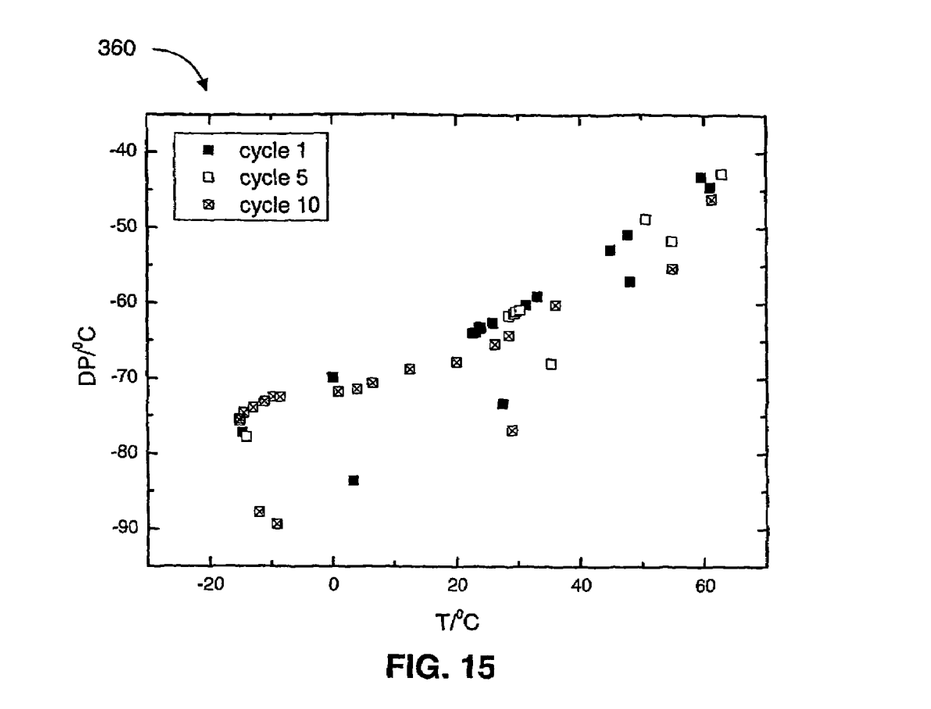
FIG. 15 is a graph of the behavior of dew point as a function of lo temperature during temperature cycling of the QCM-based humidity sensor of FIG. 2.

In another experiment, crystals were rechecked after four months at room environment, i.e.: relative humidity greater than 40% and temperature of 20° C.±5° C. Reference is now made To FIGS. 14 and 15. FIG. 14 is a graph, generally referenced 340, of the behavior of the QCM-based humidity sensor of FIG. 2 during temperature cycling. FIG. 15 is a graph, generally referenced 360, of the behavior of dew point as a function of temperature during temperature cycling of the QCM-based humidity sensor of FIG. 2. FIG. 14 represents the performance of the QCM before, during and after temperature cycling. The temperature cycling profile is: −20° C. to 70° C. at a rate of 2 degrees per minute, and two hours of exposure to the extreme temperatures at each cycle. During the temperature cycling, flow of dry nitrogen is maintained.

FIGS. 14 and 15 show no change in the behavior of the QCM crystal of the QCM-based humidity sensor before the temperature cycling (cycle 1), in the middle of temperature cycling (cycle 5), and at the end of the temperature cycling (cycle 10). It is noted that the QCM changes linearly with DP, which is itself a function of temperature.

Changes in the humidity of sealed systems are usually expected to occur over a very long time period. Such changes are typically caused by slow degassing of the inner components of a given device, or even the walls of the container. Rapid changes may be caused by one of the seals breaking, for example, or some other form of mechanical damage. These types of changes would cause catastrophic failure that would immediately show up in the overall performance, without the need for a sensitive device to measure humidity. Nevertheless, there are situations in which a fast response of the humidity sensor may be advantageous. Therefore, the time response of the coated QCM to changes in humidity should be determined.

Figure 16:
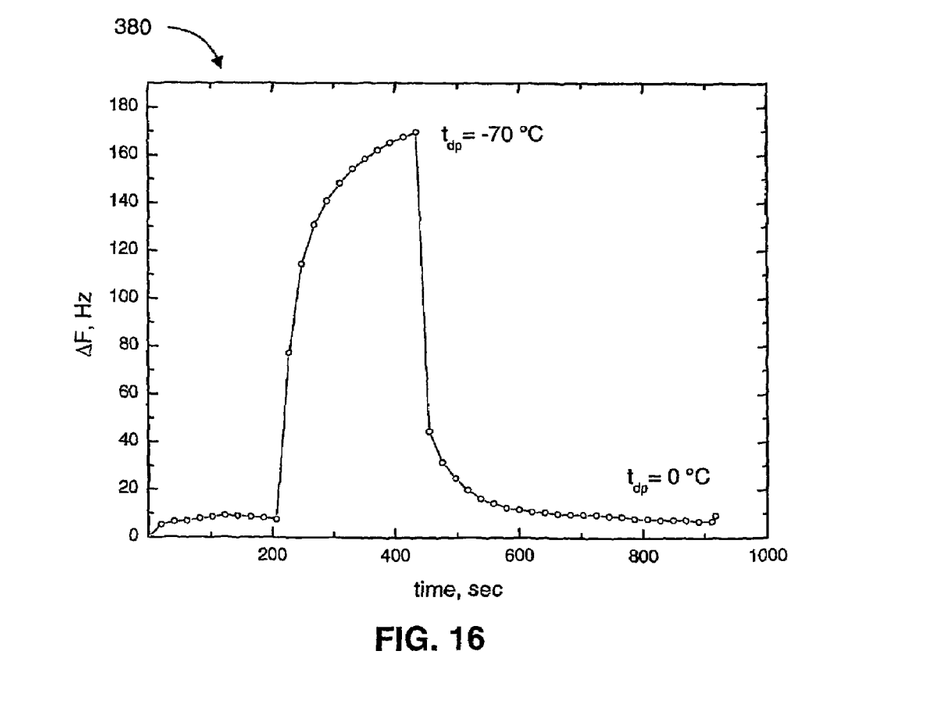
FIG. 16 is a graph of the time response of the QCM-based humidity sensor of FIG. 2 to changes in humidity.

Reference is now made to FIG. 16, which is a graph of the time response of the QCM-based humidity sensor of FIG. 2 to changes in humidity. FIG. 16 depicts typical data for the response of the QCM-based humidity sensor to changes in humidity between DP at −70° C. and at 0° C. It is noted that the response is not quite symmetrical with respect to a decrease or an increase in humidity. When the humidity is decreased, it requires over 200 seconds for the change of frequency to approach its new value. When the humidity is increased, most of the change in frequency occurs over a shorter period of less than 100 seconds. This is to be expected, considering the coating on the surface of the implementation of this humidity sensor, since it implies that the QCM could withstand cycling over a wide range of humidity, without significant changes in the properties of the coating.

It will be appreciated by persons skilled in the art that the disclosed technique is not limited to what has been particularly shown and described hereinabove. Rather the scope of the disclosed technique is defined only by the claims, which follow.

The invention claimed is:

1. A humidity sensor for measuring low humidity levels, said humidity sensor comprising a quartz crystal microbalance (QCM),
wherein a metallic surface of said QCM is electroplated with a hygroscopic layer;
wherein a salt is formed on said hygroscopic layer; and
wherein said hygroscopic layer comprises Manganese (Mn).

2. The humidity sensor according to claim 1, wherein said metallic surface comprises gold.

3. The humidity sensor according to claim 1, wherein said humidity sensor is sensitive in the range of −70° C to −10° C Dew Point.

4. The humidity sensor according to claim 1, wherein said salt comprises Manganese Chloride ($MnCl_2$).

5. A method for preparation of a QCM for a humidity sensor for measuring low humidity levels, the method comprising the procedures of:
electroplating a metallic surface of said QCM with a hygroscopic layer; and
forming a salt on said hygroscopic layer,
wherein said hygroscopic layer comprises Manganese (Mn).

6. The method according to claim 5, wherein said procedure of electroplating comprises electroplating with a highly hygroscopic inorganic compound.

7. The method according to claim 5, wherein said procedure of electroplating comprises electroplating with Manganese.

8. The method according to claim 5, wherein said procedure of forming comprises forming a salt of Manganese Chloride ($MnCl_2$).

9. The method according to claim 5, wherein said procedure of electroplating comprises preparing a solution containing 0.2M $MnCl_2$ and 1M $NH_4OH$, and plating at 0.15 Å/cm$^2$ until a metal film thickness of 8 μm is achieved.

10. The method according to claim 8, wherein said procedure of forming comprises exposing said $MnCl_2$ to wet hydrochloride (HCl) vapors formed over a solution of concentrate (fuming) solution of HCl, held at 0° C, for 5 minutes, and the procedure of drying in a vacuum at 50° C.

11. The method of according to claim 10, wherein the vapor pressure of HCl is 46 mmHg.

12. The method according to claim 10, further comprising the procedure of drying said QCM at 50° C.

13. The method according to claim 5, wherein said humidity sensor is sensitive in the range of −70° C. to −10° C. Dew Point.

* * * * *